United States Patent [19]

Nofre et al.

[11] Patent Number: 5,272,272
[45] Date of Patent: Dec. 21, 1993

[54] SWEETENING AGENTS DERIVED FROM L-GLUTAMIC ACID

[76] Inventors: Claude Nofre, 119 Cours Albert Thomas, 69003 Lyons; Jean-Marie Tinti, 5, Impasse de la Drelatière, 69680 Chassieu, both of France

[21] Appl. No.: 871,329

[22] Filed: Apr. 21, 1992

[30] Foreign Application Priority Data

Apr. 23, 1991 [FR] France .................. 91 05001

[51] Int. Cl.$^5$ .................. C07C 103/50; A23L 1/03
[52] U.S. Cl. .................. 546/289; 426/538; 426/548; 426/656
[58] Field of Search ........... 546/289; 426/548, 656, 426/538

[56] References Cited

U.S. PATENT DOCUMENTS 3,492,131 1/1968 Searle .................. 426/548
4,935,517 6/1990 Nofre et al. .................. 544/322

FOREIGN PATENT DOCUMENTS 0338946 10/1989 European Pat. Off. .
62-252754 1/1987 Japan .
62-252754 11/1987 Japan .

OTHER PUBLICATIONS

Mazur, J. Am. Chem. Soc., 91, 2684, 1969.
Patent Abstracts of Japan, vol. 12, No. 132, Apr. 1988.

*Primary Examiner*—Marianne M. Cintins
*Assistant Examiner*—Catherine S. Kilby Scalzo
*Attorney, Agent, or Firm*—Armstrong, Westerman, Hattori, McLeland & Naughton

[57] ABSTRACT

The present invention relates to novel sweetening agents. These sweetening agents have the general formula

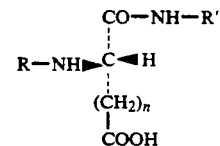

in which R is a 5,6,7,8-tetrahydro-1-naphthoyl or 1-naphthoyl radical, R' is a 2-cyanopyrid-5-yl radical and n is equal to 2. These novel sweetening agents are characterized by an extremely high sweetening potency and a very high stability compatible with all the conditions of industrial use.

4 Claims, 1 Drawing Sheet

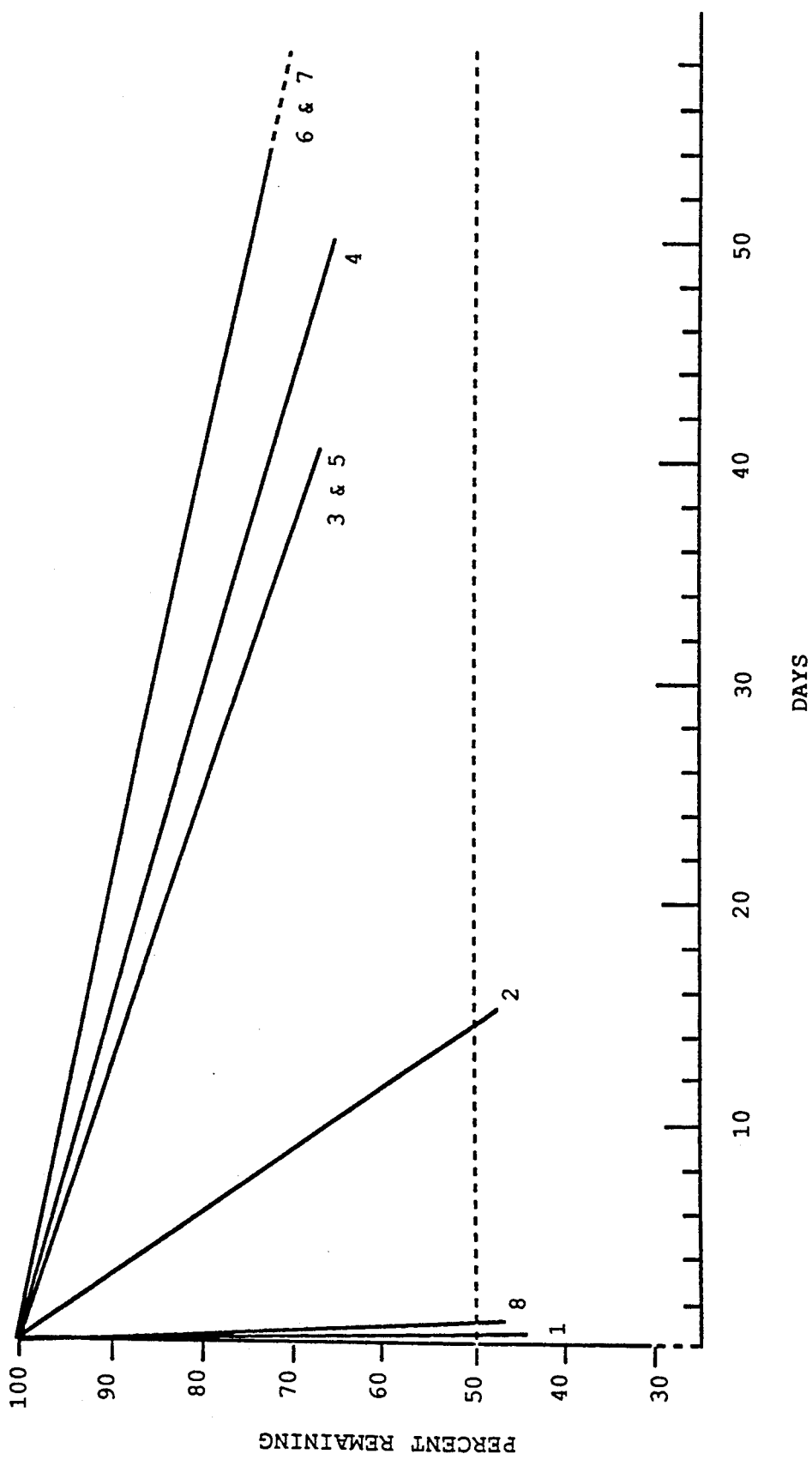
FIGURE 1 : COMPARATIVE STABILITY (pH 3, 70 °C)

SWEETENING AGENTS DERIVED FROM L-GLUTAMIC ACID

The present invention relates to novel sweetening agents derived from L-glutamic acid and to their method of preparation.

These novel sweetening agents are particularly useful for sweetening a variety of products and in particular drinks, especially fizzy drinks, foods, confectionery, pastries, chewing gums, hygiene products and toiletries, as well as cosmetic, pharmaceutical and veterinary products.

It is known that, to be usable on the industrial scale, a sweetening agent must possess firstly an intense sweetening potency, making it possible to limit the cost of use, and secondly a satisfactory stability, i.e. a stability compatible with the conditions of use.

In the particular case of fizzy drinks, which represent the principal use of sweetening agents, it is very difficult to obtain a satisfactory stability, all the more so because some of these drinks have the characteristic of being acid with a pH generally of between 2.5 and 3.5.

The document JP-A-87-252754 discloses in general terms sweetening agents of the general formula

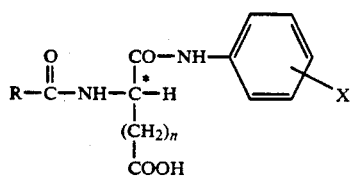

in which X is CN or $NO_2$, R is H or an alkyl, aryl, $C_1$–$C_{10}$ alkoxy or aryloxy group and n is equal to 1 or 2. The group marked with an asterisk indicates an L, D or DL configuration of the amino acid.

Of the 15 Examples specifically described, 14 compounds are aspartic acid derivatives (n=1) and only one is a glutamic acid derivative (n=2). Furthermore, the substituent X is always in the para position in these compounds. The sweetening potency (SP) of these known compounds (by comparison with a 5% solution of sucrose) is between 2 and 720 times that of sucrose (Table 1).

TABLE 1

| R | * | n | X | SP |
|---|---|---|---|---|
| H | D | 1 | CN | 110 |
| H | D | 1 | $NO_2$ | 50 |
| $CH_3O$ | L | 1 | CN | 70 |
| $CH_3O$ | D | 1 | CN | 140 |
| $C_2H_5O$ | L | 1 | CN | 80 |
| $C_6H_5O$ | L | 1 | CN | 90 |
| $C_6H_5CH_2O$ | L | 1 | CN | 260 |
| $C_6H_5CH_2O$ | D | 1 | CN | 110 |
| $C_6H_5$ | L | 1 | CN | 720 |
| $CH_3$ | D | 1 | CN | 10 |
| $C_6H_5CH_2O$ | D | 1 | $NO_2$ | 70 |
| $C_6H_5$ | L | 1 | $NO_2$ | 420 |
| $C_6H_5CH_2O$ | L | 2 | CN | 2 |
| H | L | 1 | CN | 40 |
| H | L | 1 | $NO_2$ | 2 |

Of these compounds, the one possessing the highest sweetening potency (720 times that of sucrose) is derived from L-aspartic acid and has formula (1):

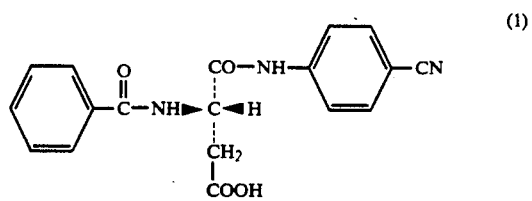

The only compound described which is derived from L-glutamic acid has formula (2):

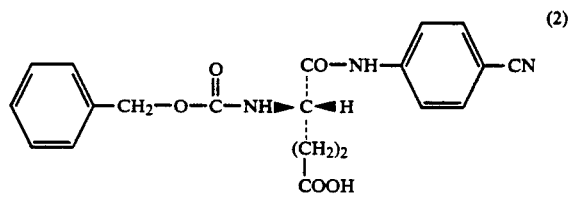

This compound possesses a very weak sweetening potency, twice that of sucrose, which excludes any possibility of its industrial application.

The document PCT/FR 90/00765, in the name of the Applicants, describes sweetening compounds which are much more potent and much more stable than those cited in the document JP-A-87-252754.

These compounds have the following general formula:

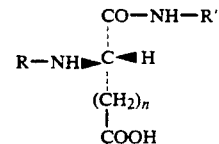

in which:
R is an acyl group of the formula

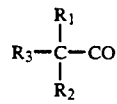

in which:

$R_1$ is a methyl, ethyl, propyl, isopropyl, phenyl, methoxy, ethoxy, trihalogenomethyl, chloro or chloromethyl radical;

$R_2$ is a hydrogen atom or a methyl, ethyl or methoxy radical;

or else $R_1$ and $R_2$, taken together with the carbon atom to which they are bonded, form a cycloalkyl group having from 3 to 6 carbon atoms; and $R_2$ is an alkyl radical having from 3 to 11 carbon atoms, an alkenyl radical having from 3 to 7 carbon atoms, a cycloalkyl radical having from 3 to 7 carbon atoms, a cycloalkyl-alkyl radical of which the cycloalkyl moiety has from 3 to 6 carbon atoms and the alkyl moiety has from 1 to 3 carbon atoms, a phenyl radical, a phenylalkyl radical of which the alkyl moiety has from 1 to 3 carbon atoms, an alkoxy radical having from 3 to 10 carbon atoms, a cycloalkoxy radical having from 3 to 6 carbon atoms, in which the two positions adjacent to carbon 1 attached to the oxygen can each be substituted by 1 or 2 methyl groups, a cycloalkylalkoxy radical of which the cycloalkyl moiety has from 3 to 6 carbon atoms and the alkoxy moiety has from 1 to 3 carbon atoms, a phenoxy radical or a phenylalkoxy radical of which the alkoxy moiety has from 1 to 3 carbon atoms;

n is equal to 1 or 2; and

R' is a group of the formula

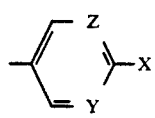

in which Y and Z, which are identical or different, are N or CH and X is selected from the group comprising CN, NO$_2$, Cl, CF$_3$, COOCH$_3$, COCH$_3$, COCF$_3$, CONH$_2$, CON(CH$_3$)$_2$, SO$_2$CH$_3$, N$_3$ and H; and their physiologically acceptable salts.

In the document PCT/FR 90/00765, 44 compounds are described and their sweetening potency can be as much as 25,000 times that of sucrose (Table 2).

TABLE 2

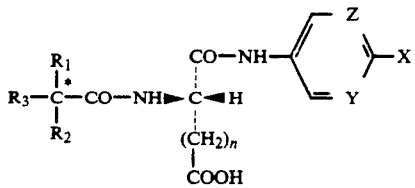

| R$_1$ | R$_2$ | R$_3$ | * | n | Y | Z | X | SP |
|---|---|---|---|---|---|---|---|---|
| CH$_3$ | H | CH$_3$(CH$_2$)$_2$ | R | 2 | CH | CH | CN | 500 |
| CH$_3$ | H | CH$_3$(CH$_2$)$_2$ | S | 2 | CH | CH | CN | 2800 |
| CH$_3$ | H | CH$_3$(CH$_2$)$_3$ | R | 2 | CH | CH | CN | 3000 |
| CH$_3$ | H | CH$_3$(CH$_2$)$_3$ | S | 2 | CH | CH | CN | 9000 |
| CH$_3$ | H | (CH$_3$)$_2$CH(CH$_2$)$_2$ | RS | 2 | CH | CH | CN | 6000 |
| CH$_3$ | H | CH$_3$(CH$_2$)$_4$ | RS | 2 | CH | CH | CN | 1000 |
| CH$_3$ | H | C$_6$H$_5$ | R | 2 | CH | CH | CN | 1300 |
| CH$_3$ | H | C$_6$H$_5$ | S | 2 | CH | CH | CN | 1500 |
| CH$_3$ | H | CH$_3$(CH$_2$)$_3$ | R | 2 | N | CH | CN | 2000 |
| CH$_3$ | H | CH$_3$(CH$_2$)$_3$ | S | 2 | N | CH | CN | 20000 |
| CH$_3$ | H | C$_6$H$_5$ | R | 2 | N | CH | CN | 2500 |
| CH$_3$ | H | C$_6$H$_5$ | S | 2 | N | CH | CN | 4000 |
| CH$_3$ | H | c-C$_6$H$_{11}$ | RS | 2 | CH | CH | CN | 1000 |
| C$_2$H$_5$ | H | CH$_3$(CH$_2$)$_3$ | RS | 2 | CH | CH | CN | 5000 |
| C$_2$H$_5$ | H | C$_6$H$_5$ | RS | 2 | CH | CH | CN | 2700 |
| C$_6$H$_5$ | H | C$_6$H$_5$ |  | 2 | CH | CH | CN | 250 |
| CH$_3$O | H | C$_6$H$_5$ | RS | 2 | CH | CH | CN | 2300 |
| CH$_3$O | H | C$_6$H$_5$ | R | 2 | N | CH | CN | 11000 |
| CH$_3$O | H | C$_6$H$_5$ | S | 2 | N | CH | CN | 3000 |
| CH$_3$O | H | CH$_3$(CH$_2$)$_3$ | RS | 2 | N | CH | CN | 2000 |
| CH$_3$ | H | C$_6$H$_5$O | RS | 2 | CH | CH | CN | 4000 |
| CH$_3$ | H | CH$_3$(CH$_2$)$_2$O | R | 2 | CH | CH | CN | 400 |
| CH$_3$ | H | CH$_3$(CH$_2$)$_2$O | S | 2 | CH | CH | CN | 200 |
| CH$_3$ | H | (2,6-diMe)-c-C$_6$H$_9$O | RS | 2 | CH | CH | CN | 1000 |
| CH$_3$ | H | C$_6$H$_5$O | RS | 2 | N | CH | CN | 13000 |
| CH$_3$ | H | C$_6$H$_5$O | R | 2 | N | CH | CN | 25000 |
| Cl | H | C$_6$H$_5$ | RS | 2 | CH | CH | CN | 2200 |
| CF$_3$ | CH$_3$O | C$_6$H$_5$ | S | 2 | CH | CH | CN | 600 |
| CH$_3$ | CH$_3$ | CH$_2$=CHCH$_2$ |  | 2 | CH | CH | CN | 500 |
| CH$_3$ | CH$_3$ | CH$_3$(CH$_2$)$_3$ |  | 2 | CH | CH | CN | 11000 |
| CH$_3$ | CH$_3$ | (CH$_3$)$_2$CH(CH$_2$)$_2$ |  | 2 | CH | CH | CN | 10000 |
| CH$_3$ | CH$_3$ | (CH$_3$)$_3$CH(CH$_2$)$_2$ |  | 2 | CH | CH | CN | 4000 |
| CH$_3$ | CH$_3$ | CH$_3$(CH$_2$)$_3$ |  | 2 | N | CH | CN | 22000 |
| CH$_3$ | CH$_3$ | CH$_3$(CH$_2$)$_4$ |  | 2 | N | CH | CN | 3000 |
| CH$_2$—CH$_2$ |  | C$_6$H$_5$ |  | 2 | CH | CH | CN | 2500 |
| CH$_2$(CH$_2$)$_2$CH$_2$ |  | C$_6$H$_5$ |  | 2 | CH | CH | CN | 2000 |
| CH$_2$(CH$_2$)$_2$CH$_2$ |  | C$_6$H$_5$ |  | 2 | N | CH | CN | 3000 |
| CH$_2$—CH$_2$ |  | C$_6$H$_5$ |  | 1 | CH | CH | CN | 1000 |
| CH$_3$ | H | CH$_3$(CH$_2$)$_3$ | RS | 1 | CH | CH | CN | 1500 |
| CH$_3$ | H | C$_6$H$_5$O | R | 1 | CH | CH | CN | 18000 |
| CH$_3$ | H | CHJ$_3$(CH$_2$)$_3$ | S | 2 | CH | CH | COCH$_3$ | 300 |
| CH$_3$ | H | CH$_3$(CH$_2$)$_3$ | S | 2 | CH | CH | CONH$_2$ | 700 |
| CH$_3$ | CH$_3$ | CH$_3$(CH$_2$)$_3$ |  | 2 | N | CH | Cl | 600 |
| CH$_3$ | H | CH$_3$(CH$_2$)$_3$ | S | 2 | N | N | CN | 10000 |

The compounds described as preferred compounds in this document PCT/FR 90/00765 have formulae (3), (4) and (5) below:

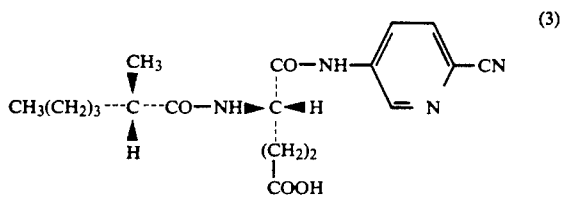

(3)

-continued

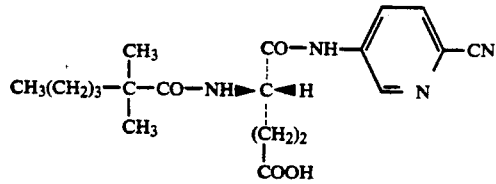
(4)

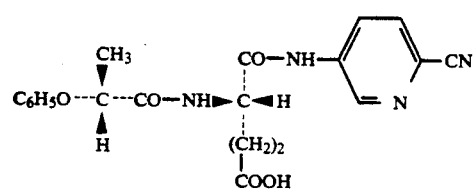
(5)

The compound of formula (3) has a sweetening potency of 20,000 times that of sucrose (compared with a 2% solution of sucrose) and a stability, evaluated by its half-life, of about 60 days at 70° C. and at pH 3.

The compound of formula (4) has a sweetening potency of 22,000 times that of sucrose and a half-life of about 70 days at pH 3 and at 70° C.

The compound of formula (5) has a sweetening potency of 25,000 times that of sucrose and a half-life of about 60 days at pH 3 and at 70° C.

Thus the preferred compounds according to said document of the prior art can be represented by the following general formula:

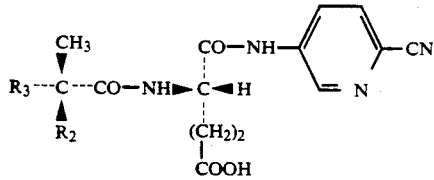

in which $R_2$ is H or $CH_3$ and $R_3$ is $C_4H_9$ when $R_2$ is H or $CH_3$, and $C_6H_5O$ when $R_2$ is H.

These compounds are characterized by high sweetening potencies of between 20,000 and 25,000 and by a high stability (half-life of about 60 to 70 days at pH 3 and at 70° C.).

The object of the present invention is to provide novel sweetening agents, derived from L-glutamic acid, which are even more potent and more stable than those described in the prior art.

These sweetening agents have the following general formula:

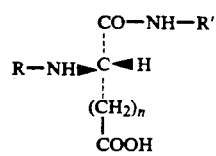

in which R is a 5,6,7,8-tetrahydro-1-naphthoyl radical of the formula

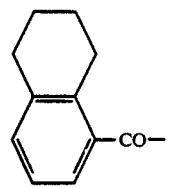

or a 1-naphthoyl radical of the formula

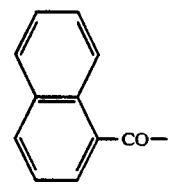

R' is a 2-cyanopyrid-5-yl radical of the formula and n is equal to 2.

In other words, the aim of the invention is to cover the two compounds of formulae (6) and (7) below:

(6)

(7)

The compound of formula (6) has a sweetening potency, on a weight basis, of 40,000 times that of sucrose (by comparison with a 2% solution of sucrose) and a stability, evaluated by its half-life at pH 3 and at 70° C., of the order of 100 days.

The compound of formula (7) has a sweetening potency, on a weight basis, of 30,000 times that of sucrose (by comparison with a 2% solution of sucrose) and a stability, evaluated by its half-life at pH 3 and at 70° C., also of the order of 100 days.

The invention is therefore the result of selecting from the state of the art two compounds derived from L-glutamic acid whose specifically chosen substituents R and R' make it possible, totally unexpectedly, to obtain for these compounds a sweetening potency which is much more intense than those of the compounds described in the prior art, thereby affording an appreciable reduction in the cost price of these compounds and hence in the cost of their use, all the more so because the acyl group R, which is formed of an ortho-fused bicyclic group, does not possess a chiral center, as is the case for compounds 3 and 5 of the prior art. The compounds of the invention also have a high stability in acid solution, which is much greater than that of the compounds described in the prior art, making it possible perfectly to satisfy the practical demands imposed by the use of sweetening agents, especially for fizzy drinks (pH 3).

To demonstrate the advantages of the compounds of the invention over the compounds of the prior art, the sweetening potency (SP) and the stability (evaluated by the half-life $t_{0.5}$ at pH 3 and at 70° C.) of the principal compounds of the prior art (compounds 1 to 5) were compared with the compounds of the present invention (compounds 6 and 7).

The results obtained have been collated in Table 3.

TABLE 3

$$\begin{array}{c} \text{CO-NH-R'} \\ | \\ \text{R-NH} \blacktriangleright \text{C} \blacktriangleleft \text{H} \\ | \\ (\text{CH}_2)_n \\ | \\ \text{COOH} \end{array}$$

| No. | R | n | R' | SP | $t_{0.5}$ (ph 3, 70° C.) |
|---|---|---|---|---|---|
| 1 | phenyl–CO– | 1 | 4-CN-phenyl | 720 | 0.33 |
| 2 | phenyl–CH$_2$OCO– | 2 | 4-CN-phenyl | 2 | 15 |
| 3 | CH$_3$(CH$_2$)$_3$CH(CH$_3$)CO– | 2 | 5-CN-pyridin-2-yl | 20 000 | 60 |
| 4 | CH$_3$(CH$_2$)$_3$C(CH$_3$)$_2$CO– | 2 | 5-CN-pyridin-2-yl | 22 000 | 70 |
| 5 | phenyl–OCH(CH$_3$)CO– | 2 | 5-CN-pyridin-2-yl | 25 000 | 60 |
| 6 | (5,6,7,8-tetrahydronaphthalen-1-yl)–CO– | 2 | 5-CN-pyridin-2-yl | 40 000 | 100 |
| 7 | (naphthalen-1-yl)–CO– | 2 | 5-CN-pyridin-2-yl | 30 000 | 100 |

As this Table shows, compounds 6 and 7 of the present invention have a sweetening potency of about 30 to 40 times that of compound 1, which is the most potent compound based on L-aspartic acid (n=1) described in the document JP-A-87-252754, and they have a sweetening potency of about 11,000 to 15,000 times that of compound 2, which is the only compound based on L-glutamic acid (n=2) described in this same document (comparisons made on the basis of the sweetening potencies evaluated by comparison with a 5% solution of sucrose). Finally, compounds 6 and 7 of the present invention have a sweetening potency of about 1.2 to 1.6 times that of compound 5, which is the most potent compound described in the document PCT/FR 90/00765.

As this Table also shows, compounds 6 and 7 of the present invention have a stability of about 300 times that of compound 1 of the document JP-A-87-252754, about 6 times that of compound 2 of the same document and about 1.6 times that of compound 5 of the document PCT/FR 90/00765.

Finally, it should be noted that the compounds of the invention are found to be much more potent and much more stable than aspartame (formula 8):

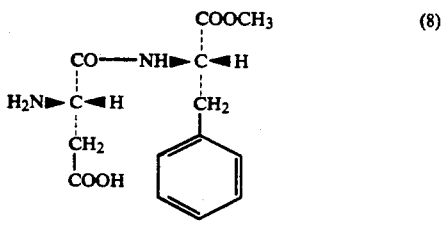

which is the most widely used synthetic sweetening agent.

The sweetening potency of aspartame is actually 180 times that of sucrose and its stability, evaluated by its half-life, is 1 day at pH 3 and at 70° C., which is tantamount to saying that compounds 6 and 7 of the present invention are about 160 to 220 times more potent and about 100 times more stable than aspartame.

Therefore, of the compounds derived from L-glutamic acid, compounds 6 and 7 of the invention are the most potent and most stable compounds described hitherto. These compounds thus combine two essential properties demanded of a good sweetening agent, namely a very high sweetening potency and a very high stability, which are found neither in the compounds of the prior art nor in aspartame.

As far as the stability is concerned, the superiority of the compounds of the invention is very clear from the diagram given in FIG. 1, which shows the curves of degradation with time, at pH 3 and at 70° C., of the compounds of the prior art (curves 1 to 5), the compounds of the present invention (curves 6 and 7) and aspartame (curve 8).

The sweetening agents of the present invention can be added to any edible product to which it is desired to give a sweet taste, provided that they are added in sufficient proportions to attain the desired level of sweetness. The optimal use concentration of the sweetening agent will depend on a variety of factors such as, for example, the sweetening potency of the sweetening agent, the conditions of storage and use of the products, the particular constituents of the products, the taste profile of the edible products and the desired level of sweetness. Any qualified person can easily determine the optimal proportion of sweetening agent which must be employed to obtain an edible product, by performing routine sensory analyses. The sweetening agents of the present invention are generally added to the edible products in proportions ranging from 0.5 mg to 10 mg of sweetening agent per kilogram or per liter of edible product, depending on the sweetening potency of the compound. The concentrated products will obviously contain larger amounts of sweetening agent and will then be diluted in accordance with the intended final uses.

The sweetening agents of the present invention can be added in pure form to the products to be sweetened, but because of their high sweetening potency, they are generally mixed with an appropriate carrier or bulking agent.

The appropriate carriers or bulking agents are advantageously selected from the group comprising polydextrose, starch, maltodextrins, cellulose, methyl cellulose, carboxymethyl cellulose and other cellulose derivatives, sodium alginate, pectins, gums, lactose, maltose, glucose, leucine, glycerol, mannitol, sorbitol, sodium bicarbonate, phosphoric, citric, tartaric, fumaric, benzoic, sorbic and propionic acids and their sodium, potassium and calcium salts, and equivalents thereof.

The present sweetening agents can be employed in an edible product either by themselves, as the only sweetening agent, or in combination with other sweetening agents such as sugars (sucrose), corn syrup, fructose, sweet dipeptide derivatives (aspartame, alitame), neohesperidin dihydrochalcone, hydrogenated isomaltulose, stevioside, the L sugars, glycyrrhizin, xylitol, sorbitol, mannitol, acesulfame-K, saccharin and its sodium, potassium, ammonium and calcium salts, cyclamic acid and its sodium, potassium and calcium salts, sucralose, monellin, thaumatin and equivalents thereof.

The compounds according to the invention can be prepared by the techniques conventionally used for peptide synthesis, especially by condensing 5,6,7,8-tetra-hydro-1-naphthoyl or 1-naphthoyl chloride with alpha-L-glutamyl-5-aminopyridine-2-carbonitrile.

1-Naphthoic acid is commercially available and 5,6,7,8-tetrahydro-1-naphthoic acid can be prepared from 1-naphthoic acid by catalytic hydrogenation in the presence of platinum oxide by the method described in J. Med. Chem., 1979, 22, 1336–1340. The acid chlorides were prepared by heating a benzene solution of the corresponding acid for 1 h at 50° C. in the presence of one equivalent of phosphorus pentachloride, and then distilled under vacuum at about 150° C.

Alpha-L-glutamyl-5-aminopyridine-2-carbonitrile is prepared by the method described in J. Med. Chem., 1973, 16, 163–166. A solution of 5.5 g (24.4 mmol) of N-trifluoroacetyl-L-glutamic anhydride and 2.6 g (21.8 mmol) of 2-cyano-5-aminopyridine (prepared according to tetrahydrofuran (20 cm³) is stirred for 12 h at 40° C. The solvent is then removed and the residue is dissolved in a 1% solution of sodium carbonate (80 cm³). The solution is rapidly washed with methylene chloride (3×30 cm³) and then acidified to pH 2–3 with a 6 N solution of HCl. Extraction with a solution of ethyl acetate (3×50 cm³), followed by drying over sodium sulfate and then evaporation of the solvent, gives 5.1 g of a crude product, N-trifluoroacetyl-alpha-L-glutamyl-5-aminopyridine-2-carbonitrile, which is obtained pure (melting point: 157° C.) after recrystallization several times from an ethanol/hexane mixture (40/60). After treatment of this compound with a 7.5% solution of ammonia for 4 h at 20° C., followed by concentration to dryness, alpha-L-glutamyl-5-aminopyridine-2-carbonitrile is finally obtained (quantitative yield, melting point: 152° C.).

N-5,6,7,8-Tetrahydro-1-naphthoyl-alpha-L-glutamyl-5-aminopyridine-2-carbonitrile (formula 6) was obtained in the following manner:

A solution of 1.91 g (0.009 mol) of 5,6,7,8-tetrahydro-1-naphthoyl chloride in anhydrous tetrahydrofuran (50 cm³) is added dropwise to a solution of 1.5 g (0.0064 mol) of alpha-L-glutamyl-5-aminopyridine-2-carbonitrile and 5.05 g (0.06 mol) of NaHCO₃ in 50 cm³ of water. After stirring for 15 minutes at 20 C., the tetrahydrofuran is removed under vacuum and the remaining aqueous solution is acidified to pH 2-3 with a 6 N solution of HCl to give a precipitate of 1.4 g of N-5,6,7,8-tetrahydro-1-naphthoyl-alpha-L-glutamyl-5-aminopyridine-2-carbonitrile (yield: 55%, melting point: 141° C. in the amorphous state) after filtration and trituration in hexane. The sweetening potency of this compound, on a weight basis, is approximately 40,000 (forty thousand) times that of sucrose by comparison with a 2% solution of sucrose, 30,000 (thirty thousand) times by comparison with a 5% solution of sucrose and 20,000 (twenty thousand) times by comparison with a 10% solution of sucrose. This is tantamount to saying that an aqueous solution of 5 mg/l of the compound has an intense sweet taste equivalent to that of a 10% solution of sucrose, corresponding to the sweetening intensities generally used in food preparations.

N-1-Naphthoyl-alpha-L-glutamyl-5-aminopyridine-2-carbonitrile (formula 7) is prepared by the same protocol as that described above, starting from 1-naphthoyl chloride and alpha-L-glutamyl-5-aminopyridine-2-carbonitrile (yield: 61%, melting point: 156° C. in the amorphous state). The sweetening potency of this compound, on a weight basis, is approximately 30,000 (thirty thousand) times that of sucrose by comparison with a 2% solution of sucrose, 22,000 (twenty-two thousand) times by comparison with a 5% solution of sucrose and 17,000 (seventeen thousand) times by comparison with a 10% solution of sucrose. This is tantamount to saying that, under these conditions, an aqueous solution of 5.9 mg/l of the compound has an intense sweet taste equivalent to that of a 10% solution of sucrose, corresponding to the sweetening intensities generally used in food preparations.

What is claimed is:

1. A compound of the formula

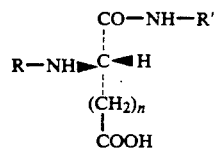

in which R is a 5,6,7,8-tetrahydro-1-naphthoyl radical of the formula

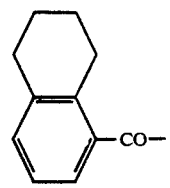

or a 1-naphthoyl radical of the formula

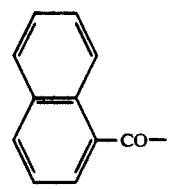

R' is a 2-cyanopyrid-5-yl radical of the formula

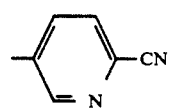

and n is equal to 2.

2. The compound of the formula

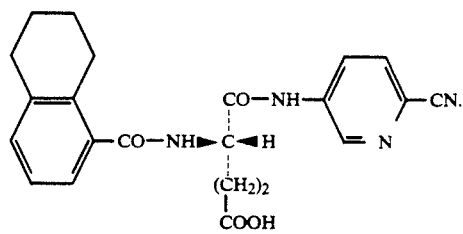

3. The compound of the formula

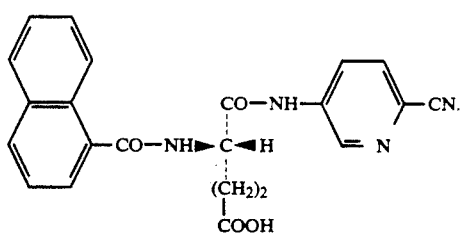

4. A sweetening agent comprising a compound according to claim 1 in combination with a carrier or bulking agent.

* * * * *